(12) United States Patent
Kadowaki et al.

(10) Patent No.: US 10,709,822 B2
(45) Date of Patent: *Jul. 14, 2020

(54) ANTITHROMBOTIC METALLIC MATERIAL

(71) Applicant: Toray Industries, Inc., Tokyo (JP)

(72) Inventors: Koji Kadowaki, Otsu (JP); Masaki Fujita, Otsu (JP); Yuka Sakaguchi, Otsu (JP); Kazuhiro Tanahashi, Otsu (JP)

(73) Assignee: Toray Industries, Inc., Tokyo (JP)

(*) Notice: Subject to any disclaimer, the term of this patent is extended or adjusted under 35 U.S.C. 154(b) by 71 days.

This patent is subject to a terminal disclaimer.

(21) Appl. No.: 15/562,324

(22) PCT Filed: Mar. 31, 2016

(86) PCT No.: PCT/JP2016/060679
§ 371 (c)(1),
(2) Date: Sep. 27, 2017

(87) PCT Pub. No.: WO2016/159243
PCT Pub. Date: Oct. 6, 2016

(65) Prior Publication Data
US 2018/0344906 A1 Dec. 6, 2018

(30) Foreign Application Priority Data
Mar. 31, 2015 (JP) ................... 2015-071588

(51) Int. Cl.
A61L 33/00 (2006.01)
A61L 33/06 (2006.01)
A61L 33/04 (2006.01)
A61L 31/10 (2006.01)

(52) U.S. Cl.
CPC .......... *A61L 33/0023* (2013.01); *A61L 31/10* (2013.01); *A61L 33/0029* (2013.01); *A61L 33/0041* (2013.01); *A61L 33/0082* (2013.01); *A61L 33/04* (2013.01); *A61L 33/064* (2013.01); *A61L 33/068* (2013.01); *A61L 2300/42* (2013.01); *A61L 2300/606* (2013.01); *A61L 2400/02* (2013.01); *A61L 2400/18* (2013.01)

(58) Field of Classification Search
None
See application file for complete search history.

(56) References Cited

U.S. PATENT DOCUMENTS

| 4,565,740 | A | * | 1/1986 | Golander | A61L 33/0029 428/409 |
| 5,672,638 | A | * | 9/1997 | Verhoeven | A61L 33/0029 424/423 |
| 5,811,151 | A | * | 9/1998 | Hendriks | A61L 27/22 427/2.24 |
| 6,200,588 | B1 | | 3/2001 | Kashiwabara et al. | |
| 6,866,113 | B2 | * | 3/2005 | Sugata | B66F 9/07568 180/253 |
| 2005/0079200 | A1 | | 4/2005 | Rathenow et al. | |
| 2006/0115514 | A1 | * | 6/2006 | Gengrinovitch | A61L 27/54 424/423 |
| 2013/0245270 | A1 | | 9/2013 | Maison et al. | |
| 2016/0067065 | A1 | | 3/2016 | Tanahashi et al. | |

FOREIGN PATENT DOCUMENTS

| JP | S5483095 | * | 2/1977 |
| JP | 2007-504920 | | 3/2007 |
| JP | 3938418 | | 6/2007 |
| JP | 2008-521476 | | 6/2008 |
| JP | 4273965 | | 6/2009 |
| JP | 2010-521246 | | 6/2010 |
| JP | 4982752 | | 7/2012 |
| JP | 2013-537883 | | 10/2013 |
| JP | 5576441 | | 8/2014 |
| KR | 2000-0059680 | | 10/2000 |
| WO | 2006/056984 | | 6/2006 |
| WO | 2008/113005 | | 9/2008 |
| WO | 2012/060544 A1 | | 5/2012 |
| WO | 2014/168198 | | 10/2014 |

OTHER PUBLICATIONS

English translation of Takagi et al. (JPS5483095 (1977.).*
Lee, SY., et al., "The effect of titanium with heparin/BMP-2 complex for improving osteoblast activity," *Carbohydr. Polym.*, 2013, vol. 98, No. 1, pp. 546-554.
Chockalingam, M., et al., "Biointerfaces on indium-tin oxide prepared from organophosphonic acid self-assembled monolayers," *Langmuir*, 2014, vol. 30, pp. 8509-8515 Abstract only.
Liu, Y., et al., "Construction of mussel-inspired coating via the direct reaction of catechol and polyethyleneimine for efficient heparin Immobilization," *Applied Surface Science*, Feb. 2015, vol. 328, pp. 163-169.
Extended European Search Report dated Dec. 3, 2018, of counterpart European Application No. 16773123.1.

* cited by examiner

*Primary Examiner* — Patricia Duffy
*Assistant Examiner* — Garen Gotfredson
(74) *Attorney, Agent, or Firm* — DLA Piper LLP (US)

(57) ABSTRACT

An antithrombogenic metallic material includes a metallic material whose surface is coated with a coating material, the coating material containing: a phosphonic acid derivative or a catechol derivative; a polymer containing, as a constituent monomer, a compound selected from the group consisting of alkyleneimines, vinylamines, allylamines, lysine, protamine, and diallyldimethylammonium chloride; and an anionic compound containing a sulfur atom and having anticoagulant activity; the polymer being covalently bound to the phosphonic acid derivative or the catechol derivative, the phosphonic acid derivative or the catechol derivative being bound to the metallic material through a phosphonic acid group or a catechol group thereof, wherein the abundance ratio of nitrogen atoms to the abundance of total atoms as measured by X-ray photoelectron spectroscopy (XPS) on the surface is 4.0 to 13.0 atomic percent.

20 Claims, No Drawings

ANTITHROMBOTIC METALLIC MATERIAL

TECHNICAL FIELD

This disclosure relates to an antithrombogenic metallic material.

BACKGROUND

Medical devices brought into contact with blood (medical equipments and medical instruments) (more specifically, artificial kidneys, artificial lungs, artificial blood vessels, artificial valves, stents, stent-grafts, catheters, free-thrombus capture devices, angioscopes, sutures, blood circuits, tubes, cannulae, blood bags, syringes, and the like) are required to have high antithrombogenicity to prevent functional deterioration due to blood coagulation.

In particular, medical devices prepared with metallic materials such as stents are likely to be recognized as foreign substances by blood, and easily cause thrombus formation.

Methods in which an anticoagulant heparin or a heparin derivative is used for coating, or chemically binding to, a surface of a metallic material to give antithrombogenicity to the metallic material have been reported. Commonly known methods in which heparin or a heparin derivative is used for coating, or chemically binding to, a surface of a metallic material include 1) methods in which the heparin or heparin derivative is immobilized by covalent bonding to a functional group introduced to the surface of the metallic material; 2) methods in which an ionic complex is formed between an organic cation mixture and the heparin or heparin derivative, and the ionic complex is dissolved in an organic solvent, followed by coating the surface of the metallic material therewith; and 3) methods in which the heparin or heparin derivative is immobilized by ionic bonding to a positively charged cationic compound introduced to the surface of the metallic material.

Reported examples of the methods of 1) include a method in which aminated heparin is covalently bound to an ozone-treated surface of a metallic material through a coupling agent and a cross-linking agent (JP 3938418 B), and a method in which heparin is immobilized on a surface of a metallic material using a coating liquid containing heparin, dopamine, cross-linking activator, and cross-linking activity aid (JP 5576441 B).

Reported examples of the methods of 2) include a method in which an ionic complex is formed between an organic cation mixture such as a quaternary ammonium salt, and heparin or a heparin derivative, and the resulting ionic complex is dissolved in an organic solvent, followed by coating a surface of a metallic material with the resulting solution (JP 4273965 B).

Reported examples of the methods of 3) include a method in which amines composed of diaminocyclohexane are introduced to a surface of a metallic material by plasma treatment, and heparin is then immobilized to the introduced amines by ionic bonding (KR 2000-0059680 A).

A method in which a negatively charged, protein non-adsorptive substance such as heparin is bound to a surface of a base material to inhibit adsorption of cells to the surface has also been reported (JP 4982752 B).

However, in the methods disclosed in JP 3938418 B and JP 5576441 B, since the heparin or heparin derivative is immobilized on the surface of the metallic material by covalent bonding to a polymer or a low molecular weight compound, the degree of freedom of the heparin or heparin derivative is decreased. It is therefore difficult to obtain the anticoagulant activity required.

In the method disclosed in JP 4273965 B, an ionic complex is formed between an organic cation mixture such as a quaternary ammonium salt, and heparin or a heparin derivative, and the resulting ionic complex is dissolved in an organic solvent, followed by coating the surface of the metallic material with the resulting solution. This method does not allow uniform coating of the metallic material surface at present since highly hydrophilic portions of the ionic complex aggregate such that they are kept away from the organic solvent, causing phase separation in the drying step after the coating. Moreover, since elution of the organic cation mixture such as a quaternary ammonium salt easily occurs when it is brought into contact with a body fluid such as blood, the elution rate of the heparin or heparin derivative cannot be controlled.

Further, KR 2000-0059680 A describes a method in which a cationic compound having an amino group is introduced to a surface of a metallic material, and heparin, which is an anionic compound having anticoagulant activity, is bound to the cationic compound by ionic bonding to achieve its immobilization. However, there is no description on an appropriate amount of the heparin or heparin derivative to be introduced. Moreover, no study has been carried out on an appropriate amount of the cationic compound to be introduced to the surface of the metallic material. When the amount of the cationic compound for coating is too small, high antithrombogenicity cannot be obtained, while in cases where the amount is too large, the compound may exhibit hemolytic toxicity.

On the other hand, as described in JP 4982752 B, it is conventionally known that attachment of heparin or the like to a base material leads to a decrease in adhesiveness of cells to the surface of the base material. Thus, when an antithrombogenic material using heparin or the like is used for an artificial blood vessel, stent, stent-graft or the like, thrombosis can be prevented, but biological incorporation of the material by adhesion/growth of endothelial cells and the like may be inhibited.

It could therefore be helpful to provide an antithrombogenic metallic material that is highly safe with its low hemolytic toxicity, and capable of maintaining high antithrombogenicity for a long period.

It could also be helpful to provide an antithrombogenic metallic material that does not decrease adhesiveness of cells to the surface while the antithrombogenicity is maintained.

SUMMARY

We thus provide:

(1) An antithrombogenic metallic material comprising a metallic material whose surface is coated with a coating material, the coating material containing:
a phosphonic acid derivative or a catechol derivative;
a polymer containing, as a constituent monomer, a compound selected from the group consisting of alkyleneimines, vinylamines, allylamines, lysine, protamine, and diallyldimethylammonium chloride; and
an anionic compound containing a sulfur atom and having anticoagulant activity;
the polymer being covalently bound to the phosphonic acid derivative or the catechol derivative, the phosphonic acid derivative or the catechol derivative being bound to the metallic material through a phosphonic acid group or a catechol group thereof, wherein the abundance ratio of nitrogen atoms to the abundance of total atoms as measured by X-ray photoelectron spectroscopy (XPS) on the surface is 4.0 to 13.0 atomic percent.

(2) The antithrombogenic metallic material according to (1), wherein the abundance ratio of sulfur atoms to the abundance of total atoms as measured by X-ray photoelectron spectroscopy (XPS) on the surface is 3.0 to 6.0 atomic percent.

(3) The antithrombogenic metallic material according to (1) or (2), wherein the polymer has a quaternary ammonium group.

(4) The antithrombogenic metallic material according to (3), wherein each carbon chain bound to the nitrogen atom in the quaternary ammonium group is constituted by an alkyl group, and the carbon number per alkyl group is 1 to 12.

(5) The antithrombogenic metallic material according to any of (1) to (4), wherein the coating material comprises: an anionic polymer containing, as a constituent monomer, a compound selected from the group consisting of acrylic acid, methacrylic acid, α-glutamic acid, γ-glutamic acid, and aspartic acid; or an anionic compound selected from the group consisting of oxalic acid, malonic acid, succinic acid, fumaric acid, glutaric acid, adipic acid, pimelic acid, suberic acid, azelaic acid, sebacic acid, malic acid, tartaric acid, and citric acid.

(6) The antithrombogenic metallic material according to any of (1) to (5), wherein the anionic compound containing a sulfur atom and having anticoagulant activity is heparin or a heparin derivative.

(7) The antithrombogenic metallic material according to any of (1) to (6), wherein the weight average molecular weight of the polymer is 600 to 2,000,000.

(8) The antithrombogenic metallic material according to any of (1) to (7), wherein the metallic material is selected from the group consisting of iron, titanium, aluminum, tin, gold, silver, copper, platinum, chromium, cobalt, nickel, zinc, and tungsten; alloys thereof; and oxides and hydroxides of these metals.

(9) An indwelling medical device produced from the antithrombogenic metallic material according to any of (1) to (8).

In the antithrombogenic metallic material, a phosphonic acid derivative or a catechol derivative is bound to a metallic surface through a phosphonic acid group or a catechol group thereof; a polymer is covalently bound to the phosphonic acid derivative or the catechol derivative; and the polymer retains an anionic compound containing a sulfur atom and having anticoagulant activity on the surface of the metallic material by ionic bonding in a state where the compound can be released. Thus, elution of components other than the anionic compound containing a sulfur atom and having anticoagulant activity can be suppressed and anticoagulant activity can be exerted for a long period while hemolytic toxicity can be kept low so that the material can be preferably applied to medical devices made of metallic materials which require antithrombogenicity (for example, stents and stent-grafts).

DETAILED DESCRIPTION

The antithrombogenic metallic material comprises a metallic material whose surface is coated with a coating material, the coating material containing:
a phosphonic acid derivative or a catechol derivative;
a polymer containing, as a constituent monomer, a compound selected from the group consisting of alkyleneimines, vinylamines, allylamines, lysine, protamine, and diallyldimethylammonium chloride; and
an anionic compound containing a sulfur atom and having anticoagulant activity;

the polymer being covalently bound to the phosphonic acid derivative or the catechol derivative, the phosphonic acid derivative or the catechol derivative being bound to the metallic material through a phosphonic acid group or a catechol group thereof, wherein the abundance ratio of nitrogen atoms to the abundance of total atoms as measured by X-ray photoelectron spectroscopy (XPS) on the surface is 4.0 to 13.0 atomic percent.

The following terms are defined as described below unless otherwise specified.

The term "antithrombogenicity" means a property that prevents blood coagulation on a surface in contact with blood. For example, "antithrombogenicity" means a property that inhibits platelet aggregation, or blood coagulation which proceeds due to, for example, activation of blood coagulation factors represented by thrombin.

The term "antithrombogenic metallic material" means a metallic material to which antithrombogenicity is given. The "antithrombogenic metallic material" may be, but does not necessarily need to be, used as a material constituting medical devices (medical equipments and medical instruments) (more specifically, stents, stent-grafts, and the like). These medical devices are brought into contact with blood, and blood coagulation is likely to proceed on surfaces of the medical devices. It is therefore said that antithrombogenic metallic materials need to be used for such devices.

The metallic material is not limited, and preferably a metal having high biocompatibility. The metallic material is preferably selected from, for example, the group consisting of iron, titanium, aluminum, tin, gold, silver, copper, platinum, chromium, cobalt, nickel, zinc, and tungsten; alloys thereof; and oxides and hydroxides of these metals. In particular, the metallic material is preferably a stainless steel such as SUS304, SUS316L, SUS420J2, or SUS630, an alloy selected from the group consisting of cobalt-chromium alloys, nickel-titanium alloys, and zinc-tungsten alloys, or a metal oxide of the alloy. The metallic material is more preferably a stainless steel such as SUS304, SUS316L, SUS420J2, or SUS630, still more preferably SUS304. The metallic material especially preferably has an oxide or a hydroxide on its surface.

The "coating material" means a material with which at least a part of the surface of the metallic material is coated, and the coating material contains: a phosphonic acid derivative or a catechol derivative; a polymer containing, as a constituent monomer, a compound selected from the group consisting of alkyleneimines, vinylamines, allylamines, lysine, protamine, and diallyldimethylammonium chloride (hereinafter referred to as "polymer constituting the coating material"); and an anionic compound containing a sulfur atom and having anticoagulant activity.

The phosphonic acid derivative constituting the coating material is an organic compound in which a phosphonic acid group ($—PO_3H_2$) is bound to a carbon atom in the compound.

The phosphonic acid derivative is not limited as long as it is a compound in which a phosphonic acid group ($—PO_3H_2$) is bound to a carbon atom of the compound. The phosphonic acid derivative is especially preferably capable of covalently binding to the polymer constituting the coating material in the present invention to stabilize the coating, thereby exerting high antithrombogenicity and suppressing elution of the polymer. The phosphonic acid derivative therefore preferably has a functional group reactive with the polymer. For example, the phosphonic acid derivative is preferably a carboxyalkylphosphonic acid or an aminoalkylphosphonic acid, more preferably a carboxyalkylphosphonic acid.

The number of carbon atoms in the carboxyalkylphosphonic acid derivative is not limited, and examples of the carboxyalkylphosphonic acid derivative include Compound A (General Formula (I)) and Compound B (General Formula (II)).

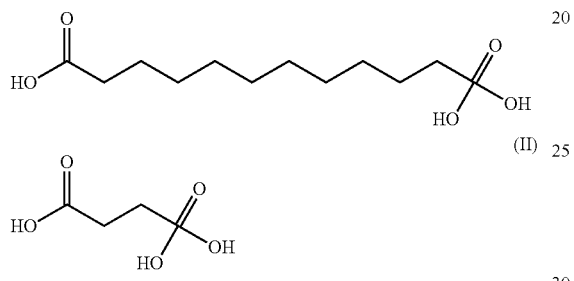

The catechol derivative constituting the coating material is an organic compound in which a catechol group represented by General Formula (III) is bound to a carbon atom in the compound.

wherein n represents an integer of 1 to 5.

The catechol derivative is not limited as long as it is a compound in which a catechol group represented by General Formula (III) is bound to a carbon atom in the compound. The catechol derivative is especially preferably capable of covalently binding to the polymer constituting the coating material in the present invention to stabilize the coating, thereby exerting high antithrombogenicity and suppressing elution of the polymer. The catechol derivative therefore preferably has a functional group reactive with the polymer. For example, the catechol derivative preferably has a terminal carboxyl group or amino group, more preferably has a terminal carboxyl group.

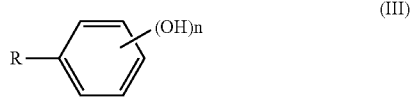

wherein n represents an integer of 1 to 5.

The number of carbon atoms in the catechol derivative is not limited, and examples of the catechol derivative include Compound C (General Formula (IV)), Compound D (General Formula (V)), Compound E (General Formula (VI)), and Compound F (General Formula (VII)).

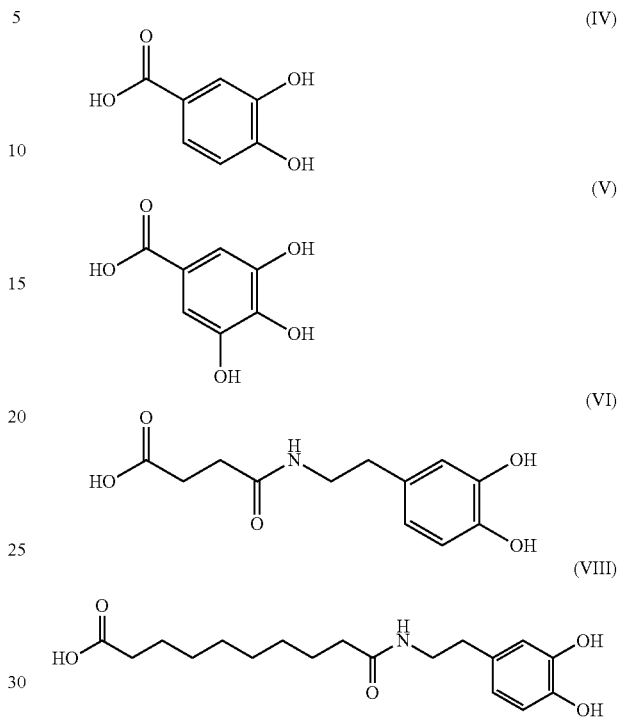

Specifically, the presence of the composition constituting the coating material on the surface of the antithrombogenic metallic material can be determined by time-of-flight secondary ion mass spectrometry (hereinafter referred to as "GCIB-TOF-SIMS").

Measurement Conditions

Apparatus: TOF.SIMS 5 (manufactured by ION-TOF GmbH)
Primary ion species: $Bi_3^{++}$
Secondary ion polarity: positive or negative
Etching ion: Ar gas cluster ion (Ar-GCIB)
Mass range (m/z): 0 to 1500
Raster size: 300 μm×300
Pixel number (each side): 128 pixels
Post-acceleration: 10 kV
Measured degree of vacuum (before sample injection): not more than $4 \times 10^{-7}$ Pa
Primary ion acceleration voltage: 30 kV
Pulse width: 5.1 ns
Bunching: Yes (high mass resolution measurement)
Charge neutralization: None Pulsed primary ions are radiated to the surface of the antithrombogenic metallic material placed in an ultrahigh vacuum, and then secondary ions released from the surface of the antithrombogenic metallic material, having a certain amount of kinetic energy, are introduced to the time-of-flight mass spectrometer. Since a mass spectrum dependent on the mass of the secondary ions is obtained, organic substances and inorganic substances present on the surface of the antithrombogenic metallic material can be identified, and information on the abundance of each substance can be obtained based on its peak intensity. By combined use of an Ar gas cluster ion beam, analysis in the depth direction can also be carried out.

The presence of the phosphonic acid derivative on the surface of the antithrombogenic metallic material can be confirmed by detection of at least one kind of peak observed by GCIB-TOF-SIMS, selected from the group consisting of the $^{31}P^-$ peak, $^{47}PO^-$ peak, $^{63}PO_2^-$ peak, $^{79}PO_3^-$ peak, $^{94}CH_3PO_3^-$ peak, $^{107}C_2H_4PO_3^-$ peak, and $^{265}C_{11}H_{22}PO_5^-$ peak, which are peaks for negative secondary ions; and the $^{65}PH_2O_2^+$ peak, $^{82}PH_3O_3^+$ peak, $^{96}CH_5PO_3^+$ peak, $^{249}C_{11}H_{22}PO_4^+$ peak, and $^{277}C_{12}H_{22}PO_5^+$ peak, which are peaks for positive secondary ions.

The presence of the catechol derivative on the surface of the antithrombogenic metallic material can be confirmed by detection of at least one kind of peak observed by GCIB-TOF-SIMS, selected from the group consisting of the $^{98}C_4H_4NO_2^-$ peak, $^{116}C_4H_6NO_3^-$ peak, $^{122}C_7H_6O_2^-$ peak, $^{135}C_8H_7O_2^-$ peak, and $^{252}C_{12}H_{14}NO_5^-$ peak, which are peaks for negative secondary ions; and the $^{137}C_8H_9O_2^+$ peak, $^{154}C_8H_{12}NO_2^+$ peak, $^{208}C_{12}H_{18}NO_2^+$ peak, and $^{254}C_{12}H_{16}NO_5^+$ peak, which are peaks for positive secondary ions.

For example, when the anionic compound containing a sulfur atom and having anticoagulant activity is heparin, the presence of the heparin on the surface of the antithrombogenic metallic material can be confirmed by detection of at least one kind of peak selected from the group consisting of the $^{80}SO_3^-$ peak, $^{97}SO_4H^-$ peak, $^{71}C_3H_3O_2^-$ peak, and $^{87}C_3H_3O_3^-$ peak, which are peaks for negative secondary ions.

For example, when the polymer constituting the coating material contains polyethyleneimine (hereinafter referred to as PEI), the presence of the PEI on the surface of the antithrombogenic metallic material can be confirmed by detection of at least one kind of peak observed by GCIB-TOF-SIMS, selected from the group consisting of the $^{18}NH_4^+$peak, $^{28}CH_2N^+$peak, $^{43}CH_3N_2^+$peak, and $^{70}C_4H_8N^+$ peak, which are peaks for positive secondary ions; and the $^{26}CN^-$ peak and $^{42}CNO^-$ peak, which are peaks for negative secondary ions.

For example, when the polymer constituting the coating material contains polyacrylic acid (hereinafter referred to as "PAA"), the presence of the PAA on the surface of the antithrombogenic metallic material can be confirmed by detection of the $^{71}C_3H_3O_2^-$ peak, which is a peak for a negative secondary ion, observed by GCIB-TOF-SIMS.

The polymer constituting the coating material is a polymer containing, as a constituent monomer, a compound selected from the group consisting of alkyleneimines, vinylamines, allylamines, lysine, protamine, and diallyldimethylammonium chloride. Since these constituent monomers have a cationic nitrogen atom, the polymer becomes cationic. On the other hand, the compound containing a sulfur atom and having anticoagulant activity is anionic, and can therefore bind to the polymer by ionic bonding. Examples of the anionic compound containing a sulfur atom and having anticoagulant activity include heparin and heparin derivatives, dextran sulfate, polyvinyl sulfonate, and polystyrene sulfonate. Heparin and heparin derivatives are more preferred. The heparin and heparin derivatives are not limited as long as blood coagulation reaction can be inhibited therewith, and examples of the heparin and heparin derivatives include heparin which is clinically generally and widely used, unfractionated heparin, and low molecular weight heparin, as well as heparins having high affinity to antithrombin III.

Since the polymer constituting the coating material has cationic properties, it may exhibit cytotoxicity and/or the like. Therefore, elution of the polymer into a body fluid such as blood is not preferred. Thus, the polymer constituting the coating material is covalently bound to a phosphonic acid derivative or catechol derivative, and the phosphonic acid derivative or catechol derivative is further bound to a surface of a metallic material through a phosphonic acid group or a catechol group of the self to achieve stable immobilization on the surface of the metallic material. On the surface of the metallic material, a metal atom is preferably covalently bound to a phosphorus atom through an oxygen atom (metal-O—P) between the metal and the phosphonic acid group, or a metal atom is preferably covalently bound to a carbon atom in the benzene ring through an oxygen atom (metal-O-Ph) between the metal and the catechol group. Confirmation of the covalent bond between the metallic material and the phosphonic acid derivative or catechol derivative is possible by observation of the fact that elution does not occur by washing with a solvent that dissolves the polymer.

The covalent bond herein means a chemical bond formed by sharing of an electron(s) between atoms. The covalent bond may be either a single bond or a multiple bond. Examples of the type of the covalent bond between the phosphonic acid derivative or catechol derivative and the polymer constituting the coating material include, but are not limited to, an amine bond, azide bond, amide bond, and imine bond. Among these, from the viewpoint of ease of formation of the covalent bond, stability after bonding and the like, an amide bond is more preferred.

The polymer constituting the coating material may be either a homopolymer or a copolymer. When the polymer is a copolymer, the copolymer may be any of a random copolymer, block copolymer, graft copolymer, and alternating copolymer. The polymer constituting the coating material is more preferably a block copolymer since, in cases of a block copolymer, stronger ionic bonding can be achieved by interaction between a block portion(s) having continuous repeat units containing nitrogen atoms, and the anionic compound containing a sulfur atom and having anticoagulant activity.

The homopolymer herein means a macromolecular compound obtained by polymerization of a single kind of constituent monomers. The copolymer herein means a macromolecular compound obtained by copolymerization of two or more kinds of monomers. The block copolymer means a copolymer having a molecular structure in which at least two kinds of polymers having different repeat units are covalently bound to each other to form a longer chain. The block means each of the "at least two kinds of polymers having different repeat units" constituting the block copolymer.

The structure of the polymer may be either linear or branched. The polymer is preferably a branched polymer since a branched polymer can form more stable ionic bonds at multiple positions with the anionic compound containing a sulfur atom and having anticoagulant activity.

The polymer has at least one functional group selected from primary to tertiary amino groups and a quaternary ammonium group. In particular, the polymer more preferably has a quaternary ammonium group rather than primary to tertiary amine groups since a quaternary ammonium group has stronger ionic interaction with the anionic compound containing a sulfur atom and having anticoagulant activity, and hence allows easier control of the elution rate of the anionic compound containing a sulfur atom and having anticoagulant activity.

The carbon numbers of the three alkyl groups constituting the quaternary ammonium group are not limited. However, when the carbon numbers are too large, hydrophobicity is high, and steric hindrance is enhanced, so that the anionic compound containing a sulfur atom and having anticoagulant activity cannot effectively bind to the quaternary ammonium group by ionic bonding. Moreover, when the carbon number is too large, cytotoxicity is more likely to occur, so that the carbon number per alkyl group bound to the nitrogen atom constituting the quaternary ammonium group is preferably 1 to 12, more preferably 2 to 6. The carbon numbers of the three alkyl groups bound to the nitrogen atom constituting the quaternary ammonium group may be the same as or different from each other.

A polyalkyleneimine is preferably used as the polymer since the amount of the anionic compound containing a sulfur atom and having anticoagulant activity adsorbed thereto by ionic interaction is large. Examples of the polyalkyleneimine include PEI, polypropyleneimines, and polybutyleneimines, as well as alkoxylated polyalkyleneimines. Among these, PEI is more preferred.

Specific examples of the PEI include "LUPASOL" (registered trademark) (manufactured by BASF), and "EPOMIN" (registered trademark) (manufactured by Nippon Shokubai Co., Ltd.). The PEI may be a copolymer with other monomers, or may be a modified body as long as the effect of the present invention is not deteriorated. The modified body herein means a polymer which has the same monomer repeat units constituting the polymer, but has partially undergone, for example, radical decomposition or recombination due to radiation irradiation.

The constituent monomers used to form the copolymer other than alkyleneimines, vinylamines, allylamines, lysine, protamine, and diallyldimethylammonium chloride are not limited, and examples of the constituent monomers include ethylene glycol, propylene glycol, vinylpyrrolidone, vinyl alcohol, vinylcaprolactam, vinyl acetate, styrene, methyl methacrylate, hydroxyethyl methacrylate, and siloxane. The content of the constituent monomers used to form the copolymer other than alkyleneimines, vinylamines, allylamines, lysine, protamine, and diallyldimethylammonium chloride is preferably not more than 10% by weight since ionic bonding with the anionic compound containing a sulfur atom and having anticoagulant activity is weak when the content is too large.

When the weight average molecular weight of the polymer constituting the coating material is too small, it becomes smaller than the molecular weight of the anionic compound containing a sulfur atom and having anticoagulant activity. Thus, stable ionic bonds cannot be formed on the surface of the metallic material so that the antithrombogenicity of interest is less likely to be obtained. On the other hand, when the weight average molecular weight of the polymer is too large, the anionic compound containing a sulfur atom and having anticoagulant activity is included in the inside of the polymer, so that the anionic compound is not exposed on the outermost surface of the coating material. Thus, the weight average molecular weight of the polymer constituting the coating material is preferably 600 to 2,000,000, more preferably 1000 to 1,500,000, still more preferably 10,000 to 1,000,000. The weight average molecular weight of the polymer can be measured by, for example, gel permeation chromatography (GPC) or the light scattering method.

The anionic compound containing a sulfur atom and having anticoagulant activity constituting the coating material is not limited as long as it can inhibit blood coagulation reaction. Examples of the compound include heparin which is clinically generally and widely used, unfractionated heparin, and low molecular weight heparin, as well as heparins having high affinity to antithrombin III, and dextran sulfate. Specific examples of the heparin include "heparin sodium" (manufactured by Organon API Inc.). The heparin or heparin derivative may be either purified or not purified.

We intensively studied ways to achieve high anticoagulant activity of the anionic compound containing a sulfur atom and having anticoagulant activity continually for a long period while elution of components other than the anionic compound containing a sulfur atom and having anticoagulant activity is suppressed. We thus discovered that there is an optimal value of the abundance ratio of sulfur atoms to the abundance of total atoms as measured by X-ray photoelectron spectroscopy (XPS) on the surface of the antithrombogenic metallic material. The abundance ratio of atoms is expressed as "atomic percent", and the atomic percent means the ratio of a specific kind of atoms to the abundance of total atoms, which is taken as 100, in terms of the number of atoms.

That is, the abundance ratio of sulfur atoms to the abundance of total atoms as measured by XPS on the surface of the antithrombogenic metallic material is preferably 3.0 to 6.0 atomic percent, more preferably 3.2 to 5.5 atomic percent, still more preferably 5.0 to 5.5 atomic percent. When the abundance ratio of sulfur atoms to the abundance of total atoms is less than 3.0 atomic percent, the coating amount of the anionic compound containing a sulfur atom and having anticoagulant activity is small and therefore, the antithrombogenicity of interest cannot be obtained. On the other hand, we found that, when the abundance ratio of sulfur atoms to the abundance of total atoms is higher than 6.0 atomic percent, the coating amount of the anionic compound containing a sulfur atom and having anticoagulant activity is sufficient, and the antithrombogenicity of interest can therefore be obtained, but that the amount of the polymer for allowing the ionic bonding needs to be large so that, as elution proceeds, a large amount of exposed polymer exhibits hemolytic toxicity due to its cationic properties.

Specifically, the abundance ratio of sulfur atoms to the abundance of total atoms on the surface of the antithrombogenic metallic material can be determined by XPS.

Measurement Conditions

Apparatus: ESCALAB 220iXL (manufactured by VG Scientific)

Excitation X-ray: monochromatic AlK a1,2 ray (1486.6 eV)

X-ray diameter: 1 mm

X-electron escape angle: 90° (the angle of the detector with respect to the surface of the antithrombogenic metallic material)

The surface of the antithrombogenic metallic material means the portion from the measurement surface to a depth of 10 nm as detected under the measurement conditions in XPS wherein the X-electron escape angle, that is, the angle of the detector with respect to the surface of the antithrombogenic metallic material, is 90°. The metallic material may or may not contain sulfur atoms. The metallic material may or may not contain nitrogen atoms.

By radiating X-ray to the surface of the antithrombogenic metallic material, and measuring the energy of photoelectrons generated therefrom, the binding energy values of bound electrons in the substance can be determined. From the binding energy values, information on the atoms on the surface of the antithrombogenic metallic material can be obtained and, from the energy shift of the peak at each binding energy value, information on the valence and the binding state can be obtained. In addition, by using the peak area ratio of each peak, quantification, that is, calculation of the abundance ratios of atoms, valences, and binding states, is possible.

Specifically, the S2p peak, which indicates the presence of sulfur atoms, appears near a binding energy value of 161 eV to 170 eV. We discovered that the area ratio of the S2p peak in the whole peak is preferably 3.0 to 6.0 atomic percent. In the calculation of the abundance ratio of sulfur atoms to the abundance of total atoms, the obtained value is rounded to one decimal place.

Similarly, by XPS measurement, we discovered that there is an optimal value of the abundance ratio of nitrogen atoms to the abundance of total atoms as measured by XPS on the surface of the antithrombogenic metallic material. That is, the abundance ratio of nitrogen atoms to the abundance of total atoms as measured by XPS on the surface of the antithrombogenic metallic material is preferably 4.0 to 13.0 atomic percent, more preferably 9.0 to 10.0 atomic percent, from the viewpoint of increasing the antithrombogenicity. When the abundance ratio of nitrogen atoms to the abundance of total atoms is not less than 4.0 atomic percent, the amount of the polymer present on the surface of the metallic material is sufficient. Accordingly, an optimal amount of ionic bonds for obtaining preferred antithrombogenicity can be obtained with the coating amount of the anionic compound containing a sulfur atom and having anticoagulant activity such as heparin or a heparin derivative which is ionically bound through the polymer. On the other hand, when the abundance ratio of nitrogen atoms to the abundance of total atoms is not more than 13.0 atomic percent, the phenomenon that the amount of the polymer present on the surface of the metallic material becomes too large, and therefore elution of the compound containing a sulfur atom and having anticoagulant activity proceeds, resulting in exposure of a large amount of the polymer and hence causing hemolytic toxicity due to its cationic properties, can be prevented.

Specifically, the N1s peak, that indicates the presence of nitrogen atoms, appears near a binding energy value of 396 eV to 403 eV. We discovered that the area ratio of the N1s peak in the whole peak is preferably 4.0 to 13.0 atomic percent. The N1s peak can be split into the n1 component (near 399 eV), which is attributed to carbon-nitrogen (hereinafter referred to as "C—N") bonds; and the n2 component (near 401 to 402 eV), attributed to ammonium salt, C—N (structure different from n1), and/or nitrogen oxide (hereinafter referred to as "NO"). The abundance ratio of each split peak component can be calculated according to Equation (1). In this calculation, the abundance ratio of nitrogen atoms and the abundance ratio of each split peak component to the abundance of total atoms are rounded to one decimal place.

$$\text{Split}_{ratio} = N1s_{ratio} \times (\text{Split}_{percent}/100) \quad (1)$$

Split$_{ratio}$: abundance ratio of each split peak component (%)

N1s$_{ratio}$: abundance ratio of nitrogen atoms to the abundance of total atoms (%)

Split$_{percent}$: ratio of each split peak component in the N1s peak (%)

The n2 component, which is attributed to NO, obtained by splitting the N1s peak indicates the presence of quaternary ammonium groups. We discovered that the ratio of the n2 component in the total component of the N1s peak, that is, Split$_{percent}$ (n2), is preferably 20 to 70 atomic percent, more preferably 25 to 65 atomic percent, still more preferably 30 to 60 atomic percent. In cases where Split$_{percent}$ (n2) is not less than 20 atomic percent, the abundance of quaternary ammonium groups is sufficient, so that the ionic interaction with the anionic compound containing a sulfur atom and having anticoagulant activity is within a preferred range. Thus, an optimal elution rate to obtain preferred antithrombogenicity can be obtained. On the other hand, when Split$_{percent}$ (n2) is not more than 70 atomic percent, the ionic interaction with the anionic compound containing a sulfur atom and having anticoagulant activity is not too strong, and a decrease in the degree of freedom due to formation of an ionic complex can be prevented. Thus, the elution rate is not too slow, and an optimal elution rate to obtain more preferred antithrombogenicity can be obtained. Because of the above reasons, the abundance ratio of the n2 component, that is, Split (n2), which is calculated according to Equation (1), is preferably 1.4 to 8.4 atomic percent, more preferably 1.8 to 7.2 atomic percent, still more preferably 2.4 to 6.0 atomic percent.

The C1s peak, which indicates the presence of carbon atoms, appears near a binding energy value of 282 to 292 eV. The C1s peak can be mainly split into the c1 component (near 285 eV), which is attributed to carbon-hydrogen (hereinafter referred to as "CHx") bonds suggesting the presence of a saturated hydrocarbon(s) and/or the like, to carbon-carbon (hereinafter referred to as "C—C") bonds, and/or to carbon-carbon (hereinafter referred to as "C=C") bonds; the c2 component (near 286 eV), which is attributed to carbon-oxygen (hereinafter referred to as "C—O") bonds suggesting the presence of an ether(s) and/or hydroxyl groups, and/or to carbon-nitrogen (hereinafter referred to as "C—N") bonds; the c3 component (near 287 to 288 eV), which is attributed to carbon=oxygen (hereinafter referred to as "C=O") bonds suggesting the presence of carbonyl groups; the c4 component (near 288 to 289 eV), which is attributed to oxygen-carbon-oxygen (hereinafter referred to as "O=C—O") bonds suggesting the presence of ester groups and/or carboxyl groups; and the c5 component (near 290 to 292 eV), which is attributed to π-π* satellite peak (hereinafter referred to as "π-π") bonds suggesting the presence of a conjugated system(s) such as benzene rings. The abundance ratio of each split peak component can be calculated according to Equation (2). In this calculation, the abundance ratio of carbon atoms and the abundance ratio of each split peak component to the abundance of total atoms are rounded to one decimal place.

$$\text{Split}_{ratio} = C1s_{ratio} \times (\text{Split}_{percent}/100) \quad (2)$$

Split$_{ratio}$: abundance ratio of each split peak component (%)

C1s$_{ratio}$: abundance ratio of carbon atoms to the abundance of total atoms (%)

Split$_{percent}$: ratio of each split peak component in the C1s peak (%)

The c3 component, which is attributed to C=O bonds, obtained by splitting the C1s peak indicates the presence of amide groups. We discovered that the ratio of the c3 component in the total component of the C1s peak, that is, the abundance ratio of amide groups as measured by XPS on the surface of the antithrombogenic metallic material, is preferably not less than 3.0 atomic percent, more preferably not less than 8.0 atomic percent, still more preferably not less than 10.0 atomic percent. In cases where the abundance ratio of the amide groups is not less than 3.0 atomic percent, occurrence of covalent bonding between the polymer constituting the coating material and the phosphonic acid derivative or catechol derivative through amide bonds is sufficient. Thus, deterioration of the state of ionic bonding with the anionic compound containing a sulfur atom and having anticoagulant activity due to the configuration of the polymer on the surface of the metallic material can be prevented, and more preferred antithrombogenicity can be obtained.

The antithrombogenic metallic material can be favorably used for medical devices, for example, medical equipments and medical instruments. The antithrombogenic metallic material is especially preferably used as a material for stents and stent-grafts.

Methods of producing the antithrombogenic metallic material are described below. For example, the coating with the coating material may be carried out by adding the metallic material of interest to a solution containing: a compound selected from the group consisting of a phosphonic acid derivative and a catechol derivative; a polymer containing, as a constituent monomer, a compound selected from the group consisting of alkyleneimines, vinylamines, allylamines, lysine, protamine, and diallyldimethylammonium chloride; and an anionic compound containing a sulfur atom and having anticoagulant activity. Alternatively, the surface of the metallic material may be coated with the coating material after entirely or partially reacting the phosphonic acid derivative or the catechol derivative, the polymer, and the anionic compound containing a sulfur atom and having anticoagulant activity.

In particular, from the viewpoint of efficiently achieving antithrombogenicity on the surface of the metallic material, a method in which a phosphonic acid derivative or a catechol derivative is bound to a surface of a metallic material through a phosphonic acid group or a catechol group of the self in a first coating step, and a polymer containing, as a constituent monomer, a compound selected from the group consisting of alkyleneimines, vinylamines, allylamines, lysine, protamine, and diallyldimethylammonium chloride, is covalently bound to the phosphonic acid derivative or catechol derivative in a second coating step, followed by binding an anionic compound containing a sulfur atom and having anticoagulant activity to the polymer by ionic bonding in a third coating step, is more preferred.

When the polymer contains a primary to tertiary amino group(s), a step of modifying the polymer with quaternary ammonium may be included after the second coating step to increase ionic interaction with the anionic compound containing a sulfur atom and having anticoagulant activity, and enable easy control of the elution rate of the anionic compound containing a sulfur atom and having anticoagulant activity.

A production method in which a phosphonic acid derivative or a catechol derivative is bound to a surface of a metallic material through a phosphonic acid group or a catechol group of the self in a first coating step, and a polymer containing, as a constituent monomer, a compound selected from the group consisting of alkyleneimines, vinylamines, allylamines, lysine, protamine, and diallyldimethylammonium chloride, is covalently bound to the phosphonic acid derivative or catechol derivative in a second coating step, followed by binding an anionic compound containing a sulfur atom and having anticoagulant activity to the polymer by ionic bonding in a third coating step, is described below.

The method of binding a phosphonic acid derivative to a surface of a metallic material through a phosphonic acid group of the self in the first coating step is not limited, and examples of the method include the following method. A metallic material is subjected to ultrasonic washing in water, acetone, and methanol in this order, and then dried under vacuum. The metallic material is immersed in a phosphonic acid derivative solution in tetrahydrofuran (hereinafter referred to as THF) at room temperature. After concentration using an evaporator, vacuum drying is carried out. After heating at 120° C., the metallic material is allowed to cool, and then subjected to ultrasonic washing in methanol, followed by washing with water and vacuum drying. Alternatively, the washed metallic material is immersed in a phosphonic acid derivative solution in ethanol at 37° C. overnight, and then washed with ethanol and water, followed by vacuum drying.

The method of binding a catechol derivative to a surface of a metallic material in the first coating step is not limited, and examples of the method include the following method. A metallic material is subjected to ultrasonic washing in water, acetone, and methanol in this order, and then dried under vacuum. The metallic material is then immersed in a catechol derivative solution in Tris-HCl buffer (pH 8.5) at room temperature. After concentration using an evaporator, vacuum drying is carried out. After heating at 120° C., the metallic material is allowed to cool, and then subjected to ultrasonic washing in water, followed by vacuum drying. Alternatively, the washed metallic material is immersed in a catechol derivative solution in Tris-HCl buffer (pH 8.5) at 37° C. overnight, and then washed with water, followed by vacuum drying.

The method of covalently binding the polymer constituting the coating material to the phosphonic acid derivative or catechol derivative is not limited. When the phosphonic acid derivative or catechol derivative has a functional group(s) (for example, hydroxyl, thiol, amino, carboxyl, aldehyde, vinyl, alkyl halide, isocyanate, and/or thioisocyanate), the polymer may be covalently bound by chemical reaction. For example, when the phosphonic acid derivative or catechol derivative has a carboxyl group and/or the like, a polymer having a hydroxyl group, thiol group, amino group, and/or the like may be covalently bound to the phosphonic acid derivative or catechol derivative. Examples of such a method include a method in which a compound having a hydroxyl group, thiol group, amino group, and/or the like is covalently bound to a polymer, and the resulting polymer is covalently bound to the phosphonic acid derivative or catechol derivative having a carboxyl group and/or the like. Another method which may be used is a method in which a phosphonic acid derivative or a catechol derivative is covalently bound to a polymer containing, as a constituent monomer, a compound selected from the group consisting of alkyleneimines, vinylamines, allylamines, lysine, protamine, and diallyldimethylammonium chloride in a first step, and the resulting polymer is bound to a surface of a metallic material through a phosphonic acid group or catechol group of the phosphonic acid derivative or catechol derivative in a second step, followed by binding an anionic compound containing a sulfur atom and having anticoagulant activity to the polymer by ionic bonding in a third coating step.

From the viewpoint of exhibiting high antithrombogenicity continually for a longer period, a first additional step in which one or both of an anionic polymer comprising, as a constituent monomer, a compound selected from the group consisting of acrylic acid, methacrylic acid, α-glutamic acid, γ-glutamic acid, and aspartic acid; and at least one anionic compound selected from the group consisting of oxalic acid, malonic acid, succinic acid, fumaric acid, glutaric acid, adipic acid, pimelic acid, suberic acid, azelaic acid, sebacic acid, malic acid, tartaric acid, and citric acid; is/are covalently bound to a polymer containing, as a constituent monomer, a compound selected from the group consisting of alkyleneimines, vinylamines, allylamines, lysine, protamine, and diallyldimethylammonium chloride, or to a phosphonic acid derivative or catechol derivative, is preferably carried out after the second coating step. More preferably, a second additional step in which an anionic polymer or an anionic compound is covalently bound to a polymer containing, as a constituent monomer, a compound selected from the group consisting of alkyleneimines, vinylamines, allylamines, lysine, protamine, and diallyldimethylammonium chloride is carried out, and then a third coating step in which an anionic compound containing a sulfur atom and having anticoagulant activity such as heparin or a heparin derivative is bound to the polymer by ionic bonding is carried out. When the polymer contains a primary to tertiary amino group(s), a step of modifying the polymer with quaternary ammonium may be included after the second additional step, in order to increase ionic interaction with the anionic compound containing a sulfur atom and having anticoagulant activity, thereby enabling easy control of the elution rate of the anionic compound containing a sulfur atom and having anticoagulant activity. If necessary, third and fourth additional steps may further be carried out using an anionic polymer, or an anionic compound and a polymer.

The anionic polymer is preferably, but does not necessarily need to be, PAA, polymethacrylic acid, poly(α-glutamic acid), poly(γ-glutamic acid), or polyaspartic acid since, in cases where the weight ratio of anionic functional groups is high, a larger coating amount can be achieved by covalent bonding with the metallic material and the phosphonic acid derivative or catechol derivative, or the polymer described above. The anionic polymer is more preferably PAA.

Specific examples of the PAA include "polyacrylic acid" (manufactured by Wako Pure Chemical Industries, Ltd.). The PAA may be a copolymer with other monomers, or may be a modified body as long as the desired effect is not deteriorated.

The anionic polymer may, but does not necessarily need to, form a copolymer with constituent monomers other than those described above. Examples of such monomers include ethylene glycol, propylene glycol, vinyl pyrrolidone, vinyl alcohol, vinyl caprolactam, vinyl acetate, styrene, methyl methacrylate, hydroxyethyl methacrylate, and siloxane. The content of the constituent monomers forming the copolymer with the anionic polymer is preferably not more than 10% by weight since, in cases where the content is too large, the amount of coating formed by covalent bonding with the metallic material and the phosphonic acid derivative or catechol derivative, or the polymer described above, is small.

When the weight average molecular weight of the anionic polymer is not less than 600, the amount of coating formed by covalent bonding with the metallic material and the polymer is favorable, so that high antithrombogenicity can be obtained. On the other hand, when the weight average molecular weight of the anionic polymer is not more than 2,000,000, the possibility that the anionic compound containing a sulfur atom and having anticoagulant activity is embedded because the size of the anionic polymer is too large can be reduced, which is preferred. Accordingly, the weight average molecular weight of the anionic polymer is preferably 600 to 2,000,000, more preferably 10,000 to 1,000,000.

The anionic compound is preferably, but does not necessarily need to be, oxalic acid, malonic acid, succinic acid, fumaric acid, glutaric acid, adipic acid, pimelic acid, suberic acid, azelaic acid, sebacic acid, malic acid, tartaric acid, or citric acid since, when the weight ratio of anionic functional groups is high, the amount of coating formed by covalent bonding with the metallic material and the phosphonic acid derivative or catechol derivative, or the polymer described above, is large. Succinic acid is more preferred.

Examples of the method for covalently binding the polymer to the phosphonic acid derivative or catechol derivative in the second coating step include a method in which condensation reaction is carried out using a dehydration-condensation agent or the like.

Examples of the type of the dehydration-condensation agent used include, but are not limited to, carbodiimide compounds such as N,N'-dicyclohexyl carbodiimide, N,N'-diisopropyl-carbodiimide, 1-ether-3-(3-dimethylaminopropyl)carbodiimide, 1-ether-3-(3-dimethylaminopropyl)carbodiimide hydrochloride (hereinafter referred to as "EDC"), 1,3-bis(2,2-dimethyl-1,3-dioxolan-4-ylmethyl)carbodiimide, N-{3-(dimethylamino)propyl-}-N'-ethylcarbodiimide, N-{3-(dimethylamino)propyl-}-N'-ethylcarbodimide methiodide, N-tert-butyl-N'-ethylcarbodiimide, N-cyclohexyl-N'-(2-morpholinoethyl)carbodiimide, meso-p-toluenesulfonate, N,N'-di-tert-butylcarbodiimide, and N,N'-di-p-tricarbodiimide; and triazine compounds such as 4-(4,6-dimethoxy-1,3,5-triazin-2-yl)-4-methylmorpholinium chloride n-hydrate (hereinafter referred to as "DMT-MM").

The dehydration-condensation agent may be used together with a dehydration-condensation promoter. Examples of the dehydration-condensation promoter used include, but are not limited to, pyridine, 4-dimethylaminopyridine (hereinafter referred to as "DMAP"), triethylamine, isopropylamine, 1-hydroxybenzotriazole, and N-hydroxysuccinimide.

The polymer constituting the coating material, the dehydration-condensation agent, and the dehydration-condensation promoter may be prepared as a mixed aqueous solution to be used for the reaction, or may be sequentially added to perform the reaction.

When the polymer constituting the coating material contains a primary to tertiary amino group(s), a step of modifying the polymer with quaternary ammonium may be included to increase ionic interaction with the anionic compound containing a sulfur atom and having anticoagulant activity, thereby enabling easy control of the elution rate of the anionic compound containing a sulfur atom and having anticoagulant activity.

Examples of the method of modifying the polymer constituting the coating material with quaternary ammonium include a method in which the polymer is modified with quaternary ammonium before being covalently bound to the phosphonic acid derivative or catechol derivative, and a method in which the modification with quaternary ammonium is carried out after covalently binding the polymer to the phosphonic acid derivative or catechol derivative. However, from the viewpoint of increasing ionic interaction between the polymer constituting the coating material and the anionic compound containing a sulfur atom and having anticoagulant activity, quaternary ammonium groups of the polymer are preferably present in the surface side of the coating material so that ionic bonding with the anionic compound containing a sulfur atom and having anticoagulant activity easily occurs. Thus, the modification with quaternary ammonium is preferably carried out after covalently binding the polymer constituting the coating material to the phosphonic acid derivative or catechol derivative. Specifically, after covalently binding the polymer constituting the coating material to the phosphonic acid derivative or catechol derivative, an alkyl halide compound such as ether chloride or ethyl bromide, or a glycidyl-containing quaternary ammonium salt, may be directly brought into contact with the polymer, or may be brought into contact with the polymer after dissolving it in an aqueous solution or an organic solvent.

The third coating step of binding the anionic compound containing a sulfur atom and having anticoagulant activity to the polymer constituting the coating material by ionic bonding is not limited. A method in which an aqueous solution of the compound is brought into contact is preferred.

The anti-factor Xa activity on the surface of the antithrombogenic metallic material was measured. The anti-factor Xa activity herein is an index indicating the degree of inhibition of the activity of factor Xa, which promotes conversion of prothrombin to thrombin. For example, when the anionic compound containing a sulfur atom and having anticoagulant activity in the antithrombogenic metallic material is heparin or a heparin derivative, its surface amount can be known in terms of the unit of anti-factor Xa activity. For the measurement, "Test Team (registered trademark) Heparin S" (manufactured by Sekisui Medical Co., Ltd.) was used. When the anti-factor Xa activity is too low, the surface amount of the heparin or heparin derivative in the antithrombogenic metallic material is small, and the antithrombogenicity of interest is less likely to be obtained. That is, the anti-factor Xa activity is preferably not less than 15 mIU/cm$^2$, more preferably not less than 30 mIU/cm$^2$, still more preferably 100 mIU/cm$^2$. The surface amount based on the anti-factor Xa activity herein means a value measured after 30 minutes of immersion in physiological saline at 37° C.

The antithrombogenic metallic material is characterized in that, irrespective of the fact that the total coating amount of the heparin or heparin derivative with which the surface of the metallic material is coated as estimated based on the anti-factor Xa activity is small, the initial surface amount of the heparin or heparin derivative after the 30 minutes of immersion in physiological saline is high. The total coating amount herein means the sum of the total amount of the heparin or heparin derivative eluted and the surface amount of the heparin or heparin derivative remaining on the surface of the antithrombogenic metallic material as measured based on the anti-factor Xa activity. When the total coating amount is too large, the coating material is thick, and the function as a stent is adversely affected, while when the total coating amount is too small, the antithrombogenicity of interest is less likely to be obtained. That is, preferably, the total coating amount as estimated based on the anti-factor Xa activity on the surface of the antithrombogenic metallic material is not more than 10,000 mIU/cm$^2$, and the initial surface amount after 30 minutes of immersion in physiological saline is not less than 15 mIU/cm$^2$. More preferably, the total coating amount is not more than 10,000 mIU/cm$^2$, and the initial surface amount after 30 minutes of immersion in physiological saline is not less than 30 mIU/cm$^2$. Still more preferably, the total coating amount is not more than 5000 mIU/cm$^2$, and the initial surface amount after 30 minutes of immersion in physiological saline is not less than 100 mIU/cm$^2$. The amount of the heparin or heparin derivative eluted herein means the amount of the heparin or heparin derivative eluted into human plasma after immersion in the human plasma at 37° C. for 24 hours. For the measurement, "Test Team (registered trademark) Heparin S" (manufactured by Sekisui Medical Co., Ltd.) was used.

Elution of the anionic compound containing a sulfur atom and having anticoagulant activity proceeds as the antithrombogenic metallic material is continuously used. In this process, the exposed polymer might exhibit hemolytic toxicity because of its cationic properties. As an index indicating the hemolytic toxicity, the hemolysis rate calculated according to Equation (3) was used. Hemolytic toxicity is ranked into different grades based on the value of the hemolysis rate as shown in Table 1, according to the hemolytic toxicity test described in a guideline published by Ministry of Health, Labour and Welfare, "Basic Principles of Biological Safety Evaluation Required for Application for Approval to Market Medical Devices". The hemolytic toxicity in the present invention is preferably ranked into the "nonhemolytic" or "mildly hemolytic" grade, more preferably ranked into the "nonhemolytic" grade.

$$\text{Hemolysis rate } (\%) = [(At-An)/(Ap-An)] \times 100 \quad (3)$$

At: absorbance of the sample
An: absorbance of the negative control
Ap: absorbance of the positive control

TABLE 1

| Hemolysis rate (%) | Grade |
| --- | --- |
| Hemolysis rate ≤ 2 | Nonhemolytic |
| 2 < Hemolysis rate ≤ 10 | Mildly hemolytic |
| 10 < Hemolysis rate ≤ 20 | Moderately hemolytic |
| 20 < Hemolysis rate ≤ 40 | Strongly hemolytic |
| 40 < Hemolysis rate | Very strongly hemolytic |

EXAMPLES

Our materials and methods are described below in detail by way of Examples and Comparative Examples. However, this disclosure is not limited thereto.

Example 1

As a metallic material, a plate material (1 cm length, 0.5 cm width) of SUS304 was used. The SUS304 was subjected to ultrasonic washing in water, acetone, and methanol in this order, and then dried under vacuum. The washed SUS304 was immersed in 1 mM Compound A (General Formula (I)) solution in ethanol at 37° C. overnight, and then washed with ethanol and water, followed by drying under vacuum to covalently bind Compound A to the surface of the SUS304 (first coating step).

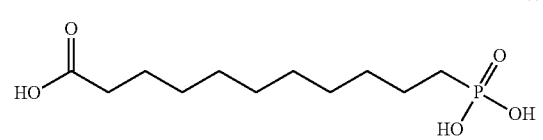

(I)

Subsequently, the SUS304 was immersed in an aqueous solution of 0.5 wt % DMT-MM (manufactured by Wako Pure Chemical Industries, Ltd.) and 5.0 wt % PEI (LUPASOL (registered trademark) P, manufactured by BASF), which is a part of the coating material, and the reaction was allowed to proceed at 30° C. for 2 hours, thereby covalently binding PEI to Compound A by condensation reaction (second coating step). The aqueous solution after the reaction was removed, and the SUS304 was washed with distilled water.

The SUS304 was further immersed in an aqueous solution of ethyl bromide (manufactured by Wako Pure Chemical Industries, Ltd.) or pentyl bromide (manufactured by Wako Pure Chemical Industries, Ltd.) in 1 wt % methanol, and the reaction was allowed to proceed at 35° C. for 1 hour and then at 50° C. for 4 hours, thereby allowing modification of PEI with quaternary ammonium (quaternary-ammonium-modification step). The aqueous solution after the reaction was removed, and the SUS304 was washed with methanol and distilled water.

Finally, the SUS304 was immersed in an aqueous solution (pH 4) of 0.75 wt % heparin sodium (manufactured by Organon API Inc.) and 0.1 mol/L sodium chloride, and the reaction was allowed to proceed at 70° C. for 6 hours, thereby allowing ionic bonding with PEI (third coating step). The aqueous solution after the reaction was removed, and the SUS304 was washed with distilled water.

SUS304 subjected to the third coating step without performing the quaternary-ammonium-modification step was provided as Sample 1; SUS304 subjected to the quaternary-ammonium-modification step using ethyl bromide was provided as Sample 2; and SUS304 subjected to the quaternary-ammonium-modification step using pentyl bromide was provided as Sample 3.

Each sample was subjected to measurement of the abundance ratios of nitrogen atoms and sulfur atoms to the abundance of total atoms on the surface by X-ray photoelectron spectroscopy (XPS), measurement of the surface amount based on the anti-factor Xa activity after 30 minutes of immersion in physiological saline, evaluation by a human whole blood test, and evaluation of hemolytic toxicity. The results are shown in Table 2. As shown in Table 2, Sample 1 showed a large surface amount based on the anti-factor Xa activity, and the activity was evaluated as (+). The capacity to inhibit thrombus formation evaluated by the human whole blood test was (+), and the hemolytic toxicity was evaluated as nonhemolytic (−). Samples 2 and 3 showed large surface amounts based on the anti-factor Xa activity, and the activity was evaluated as (++). The capacity to inhibit thrombus formation evaluated by the human whole blood test was (++), and the hemolytic toxicity was evaluated as nonhemolytic (−).

Example 2

The same operation as in Example 1 was carried out except that Compound B (General Formula (II)) was used instead of Compound A to perform the first coating step and the second coating step. The quaternary-ammonium-modification step was carried out by the same operation as in Example 1 using ethyl bromide, and the third coating step was then carried out.

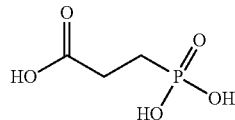
(II)

SUS304 subjected to the second coating step using PEI (LUPASOL (registered trademark) P, manufactured by BASF) was provided as Sample 4, and SUS304 subjected to the second coating step using PEI (average molecular weight, about 70,000; manufactured by Wako Pure Chemical Industries, Ltd.) was provided as Sample 5.

Each sample was subjected to measurement of the abundance ratios of nitrogen atoms and sulfur atoms to the abundance of total atoms on the surface by X-ray photoelectron spectroscopy (XPS), measurement of the surface amount based on the anti-factor Xa activity after 30 minutes of immersion in physiological saline, evaluation by a human whole blood test, and evaluation of hemolytic toxicity. The results are shown in Table 2. As shown in Table 2, Samples 4 and 5 showed large surface amounts based on the anti-factor Xa activity, and the activity was evaluated as (++). The capacity to inhibit thrombus formation evaluated by the human whole blood test was (++), and the hemolytic toxicity was evaluated as nonhemolytic (−).

Example 3

The first coating step and the second coating step were carried out by the same operation as in Example 1, and SUS304 was then immersed in an aqueous solution of 0.5 wt % DMT-MM and 0.5 wt % PAA (manufactured by Wako Pure Chemical Industries, Ltd.), followed by allowing the reaction to proceed at 30° C. for 2 hours (first additional step). The aqueous solution after the reaction was removed, and the SUS304 was washed with an aqueous sodium carbonate solution and distilled water.

The SUS304 was then immersed in an aqueous solution of 0.5 wt % DMT-MM and 5.0 wt % PEI, and the reaction was allowed to proceed at 30° C. for 2 hours (second additional step). The aqueous solution after the reaction was removed, and the SUS304 was washed with distilled water. The quaternary-ammonium-modification step was carried out using ethyl bromide by the same operation as in Example 1, and the third coating step was then carried out.

SUS304 subjected to the first coating step using Compound A, and the second additional step using PEI (average molecular weight, about 600; manufactured by Wako Pure Chemical Industries, Ltd.), was provided as Sample 6; SUS304 subjected to the first coating step using Compound A, and the second additional step using PEI (LUPASOL (registered trademark) P, manufactured by BASF) was provided as Sample 7; and SUS304 subjected to the first coating step using Compound B, and the second additional step using PEI (LUPASOL (registered trademark) P, manufactured by BASF), was provided as Sample 8.

Each sample was subjected to measurement of the abundance ratios of nitrogen atoms and sulfur atoms to the abundance of total atoms on the surface by X-ray photoelectron spectroscopy (XPS), measurement of the surface amount based on the anti-factor Xa activity after 30 minutes of immersion in physiological saline, evaluation by a human whole blood test, and evaluation of hemolytic toxicity. The results are shown in Table 2. As shown in Table 2, Samples 4 and 5 showed large surface amounts based on the anti-factor Xa activity, and the activity was evaluated as (+++). The capacity to inhibit thrombus formation evaluated by the human whole blood test was (+++), and the hemolytic toxicity was evaluated as nonhemolytic Comparative Example 1

SUS304 was subjected to ultrasonic washing in water, acetone, and methanol in this order, and then dried under vacuum. The washed SUS304 was subjected to the third coating step to bind heparin to the surface of the SUS304 by ionic bonding, to provide Sample 9.

Sample 9 was subjected to measurement of the surface amount based on the anti-factor Xa activity after 30 minutes of immersion in physiological saline, evaluation by a human whole blood test, and evaluation of hemolytic toxicity. The surface measurement by X-ray photoelectron spectroscopy (XPS) was not carried out. The results are shown in Table 2. As shown in Table 2, in Sample 9, the hemolytic toxicity was evaluated as nonhemolytic (−). However, the sample showed only a small surface amount based on the anti-factor Xa activity, and the activity was evaluated as (−). The capacity to inhibit thrombus formation evaluated by the human whole blood test was (−).

Comparative Example 2

The first coating step, the second coating step, and the quaternary-ammonium-modification step were carried out by the same operation as in Example 1, and the third coating step was then carried out.

SUS304 subjected to the first coating step using Compound B, the second additional step using PEI (average molecular weight, about 600; manufactured by Wako Pure Chemical Industries, Ltd.), and the quaternary-ammonium-modification step using ethyl bromide, was provided as Sample 10; and SUS304 subjected to the first coating step using Compound A, the second additional step using PEI (average molecular weight, about 600; manufactured by Wako Pure Chemical Industries, Ltd.), and the quaternary-ammonium-modification step using ethyl bromide, was provided as Sample 11.

Each sample was subjected to measurement of the abundance ratios of nitrogen atoms and sulfur atoms to the abundance of total atoms on the surface by X-ray photoelectron spectroscopy (XPS), measurement of the surface amount based on the anti-factor Xa activity after 30 minutes of immersion in physiological saline, evaluation by a human whole blood test, and evaluation of hemolytic toxicity. The results are shown in Table 2. As shown in Table 2, in Samples 10 and 11, the hemolytic toxicity was evaluated as nonhemolytic (−). However, the samples showed only small surface amounts based on the anti-factor Xa activity, and the activity was evaluated as (−). The capacity to inhibit thrombus formation evaluated by the human whole blood test was (−).

Comparative Example 3

The first coating step and the second coating step were carried out by the same operation as in Example 1, and SUS304 was then immersed in an aqueous solution of 0.5 wt % DMT-MM and 0.5 wt % PAA (manufactured by Wako Pure Chemical Industries, Ltd.), followed by allowing the reaction to proceed at 30° C. for 2 hours (first additional step). The aqueous solution after the reaction was removed, and the SUS304 was washed with an aqueous sodium carbonate solution and distilled water.

The SUS304 was then immersed in an aqueous solution of 0.5 wt % DMT-MM and 5.0 wt % PEI, and the reaction was allowed to proceed at 30° C. for 2 hours (second additional step). The aqueous solution after the reaction was removed, and the SUS304 was washed with distilled water.

The SUS304 was then further immersed in an aqueous solution of 0.5 wt % DMT-MM and 0.5 wt % PAA (Wako Pure Chemical Industries, Ltd.), and the reaction was allowed to proceed at 30° C. for 2 hours (third additional step). The aqueous solution after the reaction was removed, and the SUS304 was washed with an aqueous sodium carbonate solution and distilled water.

The SUS304 was then immersed in an aqueous solution of 0.5 wt % DMT-MM and 5.0 wt % PEI, and the reaction was allowed to proceed at 30° C. for 2 hours (fourth additional step). The aqueous solution after the reaction was removed, and the SUS304 was washed with distilled water. The quaternary-ammonium-modification step was carried out using a dodecane bromide solution in methanol by the same operation as in Example 1, and the third coating step was then carried out.

SUS304 subjected to the fourth additional step using PEI (LUPASOL (registered trademark) P, manufactured by BASF) was provided as Sample 12, and SUS304 subjected to the fourth additional step using PEI (average molecular weight, about 70,000; manufactured by Wako Pure Chemical Industries, Ltd.) was provided as Sample 13.

Each sample was subjected to measurement of the abundance ratios of nitrogen atoms and sulfur atoms to the abundance of total atoms on the surface by X-ray photoelectron spectroscopy (XPS), measurement of the surface amount based on the anti-factor Xa activity after 30 minutes of immersion in physiological saline, evaluation by a human whole blood test, and evaluation of hemolytic toxicity. The results are shown in Table 2. As shown in Table 2, Samples 11 and 12 showed large surface amounts based on the anti-factor Xa activity, and the activity was evaluated as (+++). The capacity to inhibit thrombus formation evaluated by the human whole blood test was (+++), but the hemolytic toxicity was evaluated as mildly hemolytic (+).

Comparative Example 4

SUS304 on which heparin was immobilized using the method disclosed in JP 5576441 B was provided as Sample 14.

Sample 14 was subjected to measurement of the surface amount based on the anti-factor Xa activity after 30 minutes of immersion in physiological saline, evaluation by a human whole blood test, and evaluation of hemolytic toxicity. The surface measurement by X-ray photoelectron spectroscopy (XPS) was not carried out. The results are shown in Table 2. As shown in Table 2, in Sample 9, the hemolytic toxicity was evaluated as nonhemolytic (−). However, the sample showed only a small surface amount based on the anti-factor Xa activity, and the activity was evaluated as (−). The capacity to inhibit thrombus formation evaluated by the human whole blood test was (−).

Example 4

In the first coating step, Compound C (the following General Formula IV), Compound D (the following General Formula (V)), Compound E (the following General Formula (VI)), or Compound F (the following General Formula (VII)), was used instead of Compound A. The washed SUS304 was immersed in a solution of 1 mM Compound C, Compound D, Compound E, or Compound F, respectively, in Tris-HCl buffer (pH 8.5) at 37° C. overnight, followed by washing with water and vacuum drying (first coating step). The same operation as in Example 1 was carried out except for the first coating step. The second coating step was carried out. The quaternary-ammonium-modification step was carried out using ethyl bromide or pentyl bromide, and the third coating step was then carried out.

SUS304 subjected to the first coating step using Compound C (the following General Formula IV), the second coating step using PEI (LUPASOL (registered trademark) P, manufactured by BASF), and the quaternary-ammoniummodification step using ethyl bromide, was provided as Sample 15; SUS304 subjected to the first coating step using Compound D (the following General Formula V), the second coating step using PEI (LUPASOL (registered trademark) P, manufactured by BASF), and the quaternary-ammonium-modification step using ethyl bromide, was provided as Sample 16; SUS304 subjected to the first coating step using Compound E (General Formula VI), the second coating step using PEI (average molecular weight, 10,000, manufactured by Wako Pure Chemical Industries, Ltd.), and the quaternary-ammonium-modification step using pentyl bromide, was provided as Sample 17; and SUS304 subjected to the first coating step using Compound F (General Formula VII), the second coating step using PEI (average molecular weight, about 70,000, manufactured by Wako Pure Chemical Industries, Ltd.), and the quaternary-ammonium-modification step using pentyl bromide, was provided as Sample 18.

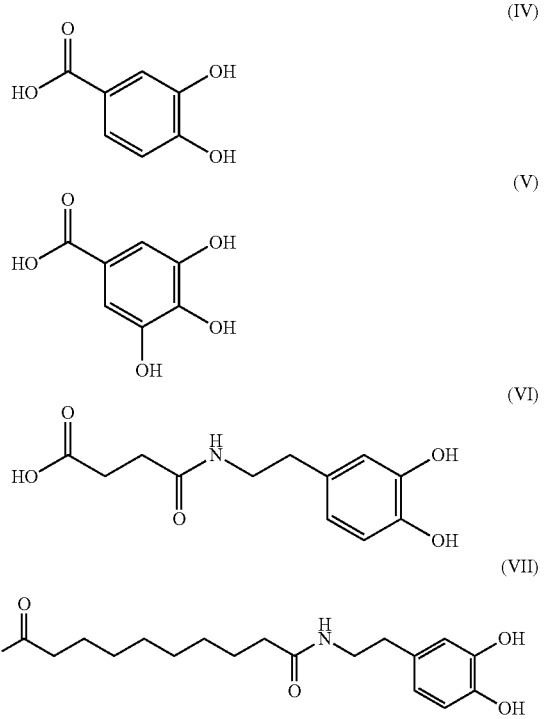

Each sample was subjected to measurement of the abundance ratios of nitrogen atoms and sulfur atoms to the abundance of total atoms on the surface by X-ray photoelectron spectroscopy (XPS), measurement of the surface amount based on the anti-factor Xa activity after 30 minutes of immersion in physiological saline, evaluation by a human whole blood test, and evaluation of hemolytic toxicity. The results are shown in Table 2. As shown in Table 2, Samples 15, 16, 17, and 18 showed large surface amounts based on the anti-factor Xa activity, and the activity was evaluated as (++). The capacity to inhibit thrombus formation evaluated by the human whole blood test was (++), and the hemolytic toxicity was evaluated as nonhemolytic (−).

Example 5

In the first coating step, Compound C or Compound E was used instead of Compound A or Compound B. The washed SUS304 was immersed in a solution of 1 mM Compound C or Compound E, respectively, in Tris-HCl buffer (pH 8.5) at 37° C. overnight, followed by washing with water and vacuum drying (first coating step). The same operation as in Example 3 was carried out except for the first coating step. The second coating step, the first additional step, and the second additional step were carried out. The quaternary-ammonium-modification step was carried out using ethyl bromide, and the third coating step was then carried out.

SUS304 subjected to the first coating step using Compound C, and the second additional step using PEI (average molecular weight, about 70,000; manufactured by Wako Pure Chemical Industries, Ltd.), was provided as Sample 19; and SUS304 subjected to the first coating step using Compound E, and the second additional step using PEI (average molecular weight, about 70,000; manufactured by Wako Pure Chemical Industries, Ltd.), was provided as Sample 20.

Each sample was subjected to measurement of the abundance ratios of nitrogen atoms and sulfur atoms to the abundance of total atoms on the surface by X-ray photoelectron spectroscopy (XPS), measurement of the surface amount based on the anti-factor Xa activity after 30 minutes of immersion in physiological saline, evaluation by a human whole blood test, and evaluation of hemolytic toxicity. The results are shown in Table 2. As shown in Table 2, Samples 19 and 20 showed large surface amounts based on the anti-factor Xa activity, and the activity was evaluated as (+++). The capacity to inhibit thrombus formation evaluated by the human whole blood test was (+++), and the hemolytic toxicity was evaluated as nonhemolytic (−).

Comparative Example 5

In the first coating step, Compound C or Compound E was used instead of Compound A or Compound B. The washed SUS304 was immersed in a solution of 1 mM Compound C or Compound E, respectively, in Tris-HCl buffer (pH 8.5) at 37° C. overnight, followed by washing with water and vacuum drying (first coating step). The same operation as in Comparative Example 2 was carried out except for the first coating step. The second coating step, the quaternary-ammonium-modification step, and the third coating step were carried out.

SUS304 subjected to the first coating step using Compound C was provided as Sample 21; and SUS304 subjected to the first coating step using Compound E was provided as Sample 22.

Each sample was subjected to measurement of the abundance ratios of nitrogen atoms and sulfur atoms to the abundance of total atoms on the surface by X-ray photoelectron spectroscopy (XPS), measurement of the surface amount based on the anti-factor Xa activity after 30 minutes of immersion in physiological saline, evaluation by a human whole blood test, and evaluation of hemolytic toxicity. The results are shown in Table 2. As shown in Table 2, in Samples 21 and 22, the hemolytic toxicity was evaluated as nonhemolytic (−). However, the samples showed only small surface amounts based on the anti-factor Xa activity, and the activity was evaluated as (−). The capacity to inhibit thrombus formation evaluated by the human whole blood test was (−).

Comparative Example 6

In the first coating step, Compound C or Compound E was used instead of Compound A. The washed SUS304 was immersed in a solution of 1 mM Compound C or Compound E, respectively, in Tris-HCl buffer (pH 8.5) at 37° C. overnight, followed by washing with water and vacuum drying (first coating step). The same operation as in Comparative Example 3 was carried out except for the first coating step. The second coating step, the first additional step, the second additional step, the third additional step, the fourth additional step, the quaternary-ammonium-modification step, and the third coating step were carried out.

SUS304 subjected to the first coating step using Compound C, and the fourth additional step using PEI (LUPASOL (registered trademark) P, manufactured by BASF), was provided as Sample 23; and SUS304 subjected to the first coating step using Compound E, and the fourth additional step using PEI (average molecular weight, about 70,000; manufactured by Wako Pure Chemical Industries, Ltd.), was provided as Sample 24.

Each sample was subjected to measurement of the abundance ratios of nitrogen atoms and sulfur atoms to the abundance of total atoms on the surface by X-ray photoelectron spectroscopy (XPS), measurement of the surface amount based on the anti-factor Xa activity after 30 minutes of immersion in physiological saline, evaluation by a human whole blood test, and evaluation of hemolytic toxicity. The results are shown in Table 2. As shown in Table 2, Samples 23 and 24 showed large surface amounts based on the anti-factor Xa activity, and the activity was evaluated as (+++). The capacity to inhibit thrombus formation evaluated by the human whole blood test was (+++), but the hemolytic toxicity was evaluated as mildly hemolytic (+).

The samples described in Examples 1 to 5 were subjected to evaluation by a cell adhesiveness test. The results are shown in Table 3. As shown in Table 3, Samples 1 to 5 and 15 to 18 were evaluated as (—H—) in terms of the cell adhesiveness. Samples 6 to 8, 19, and 20 were evaluated as (+) in terms of the cell adhesiveness.

Similarly, the samples described in Comparative Examples 1 to 6 were subjected to evaluation by a cell adhesiveness test. Samples 9 to 11, 21 and 22 were evaluated as (++) in terms of the cell adhesiveness. Samples 12 to 14, 23, and 24 were evaluated as (−) in terms of the cell adhesiveness.

In relation to antithrombogenicity and safety of our metallic material, the method of evaluation of the surface amount based on the anti-factor Xa activity, the method of evaluation by the human whole blood test, and the method of evaluation of hemolytic toxicity were as described below.

Further, in relation to the cell adhesiveness of our metallic material, the evaluation method by the cell adhesiveness test, in which the amount of adhering cells after culture was measured by the absorbance, was as described below.

Evaluation 1: Surface Amount Based on Anti-factor Xa Activity

Each sample of the antithrombogenic metallic material was cut into a piece having a size of 0.5×0.5 cm, and the piece was washed with physiological saline at 37° C. for 30 minutes. The washed sample was reacted according to the procedure for "Test Team (registered trademark) Heparin S" (manufactured by Sekisui Medical Co., Ltd.), and the absorbance at 405 nm was measured using a microplate reader (MTP-300, manufactured by Corona Electric Co., Ltd.). A calibration curve was prepared according to the procedure for "Test Team (registered trademark) Heparin S" (manufactured by Sekisui Medical Co., Ltd.) to calculate the surface amount based on the anti-factor Xa activity. The larger the surface amount, the better. The surface amount is preferably not less than 15 mIU/cm², more preferably not less than 30 mIU/cm², still more preferably not less than 100 mIU/cm². When the surface amount was less than 15 mIU/cm², the surface amount was evaluated as (−), which indicates a small surface amount; when the surface amount was not less than 15 mIU/cm², the surface amount was evaluated as (+), that indicates a larger surface amount; when the surface amount was not less than 30 mIU/cm², the surface amount was evaluated as (—H—), that indicates a still larger surface amount; and when the surface amount was not less than 100 mIU/cm², the surface amount was evaluated as (+), that indicates an even larger surface amount.

Evaluation 2 Human Whole Blood Test

Each sample of the antithrombogenic metallic material was cut into a piece having a size of 1.0×0.5 cm. The same kind of metallic material not coated with the coating material (positive control) was cut into a piece having a size of 1.0×0.5 cm. Each piece was washed with physiological saline at 37° C. for 30 minutes, and then placed in a 2-mL microtube. After adding Heparin Sodium Injection (manufactured by Ajinomoto Pharmaceuticals Co., Ltd.) to fresh human blood to a concentration of 0.4 U/mL, 2 mL of the resulting human blood was added to the microtube, and the microtube was then incubated at 37° C. for 2 hours. After the incubation, SUS304 was removed, and subjected to measurement of the concentration of thrombin-antithrombin complex (hereinafter referred to as TAT) in the blood. As shown in Equation (4), the capacity to inhibit thrombus formation was calculated.

$$\text{Capacity to inhibit thrombus formation} = Ct/Cpre \qquad (4)$$

Ct: concentration measured after the incubation of the sample (ng/mL)

Cpre: concentration measured before the incubation of the sample (ng/mL)

When the capacity to inhibit thrombus formation calculated according to Equation (4) was not less than 300, the capacity to inhibit thrombus formation was evaluated as (−), that indicates a weak capacity to inhibit thrombus formation; when the capacity was not less than 100 and less than 300, the capacity was evaluated as (+), that indicates a stronger capacity to inhibit thrombus formation; when the capacity was not less than 50 and less than 100, the capacity was evaluated as (++), that indicates a still stronger capacity to inhibit thrombus formation; and when the capacity was less than 50, the capacity was evaluated as (+++), that indicates an even stronger capacity to inhibit thrombus formation.

Evaluation 3: Hemolytic Toxicity Test

Fresh human blood was fed into an Erlenmeyer flask containing glass beads, such that the blood flowed along the wall surface of the flask. The flask was then placed on a palm, and horizontally shaken in a circular motion at a rate of about two rotations per second for about 5 minutes, to prepare defibrinated blood. Each sample of the antithrombogenic metallic material was cut into a piece having a size of 1.0×0.5 cm. The piece was washed with physiological saline at 37° C. for 30 minutes, and then placed in a 2-mL microtube. To the microtube containing the metallic material, 1 mL of the defibrinated blood after 50-fold dilution with physiological saline was added, and the tube was then incubated at 37° C. for 4 hours. Thereafter, the microtube was centrifuged at 750 G for 5 minutes. The resulting supernatant was collected, and subjected to measurement of the UV absorbance at 576 nm. When the value calculated according to Equation (3) was larger than 2, that is, when the material was hemolytic, the material was evaluated as (+), while when the value was not more than 2, that is, when the material was nonhemolytic, the material was evaluated as (−). Since the material preferably has no hemolytic toxicity, the material is preferably nonhemolytic.

Evaluation 4: Cell Adhesiveness Test

The cell adhesiveness is a property indicating a tendency to allow adhesion of cells to a material, and can be measured by the following evaluation method. Each sample of the antithrombogenic metallic material was cut into a piece having a size of 1.0×0.5 cm, and placed in a well of a 24-well microplate for cell culture (manufactured by Sumitomo Bakelite Co., Ltd.) such that the inner-wall side was facing upward, and a metal pipe-shaped weight having a thickness of 1 mm was placed on the top of the sample. To each well, normal human umbilical vein endothelial cells (Takara Bio Inc.) suspended in 2% FBS endothelial cell medium kit-2 (manufactured by Takara Bio Inc.) were added such that the well contained $4 \times 10^4$ cells. The cells were cultured in 1 mL of the medium at 37° C. under an environment of 5% $CO_2$ for 24 hours. After rinsing with PBS(−) (manufactured by Nissui Pharmaceutical Co., Ltd.), 100 pt of Cell Counting Kit-8 (manufactured by Dojindo Laboratories) was added thereto, and the cells were cultured at 37° C. under an environment of 5% $CO_2$ for 4 hours. Subsequently, the absorbance at 450 nm was measured using a microplate reader (MTP-300, manufactured by Corona Electric Co., Ltd.), followed by calculation of the absorbance as shown by Equation (5).

$$As = At - Ab \quad (5)$$

At: measured absorbance
Ab: absorbance of the blank solution (medium, and the solution of Cell Counting Kit-8; containing no cells)
As: absorbance calculated As shown in Equation (6), the cell adhesiveness was calculated.

$$\text{Cell adhesiveness (\%)} = As \text{ (sample)} \times 100 / As \text{ (control)} \quad (6)$$

As (sample): absorbance calculated after incubation of the sample
As (control): absorbance calculated after incubation of the same kind of metallic material not coated with the coating material (positive control)

Cell adhesiveness score was determined based on the cell adhesiveness (%). Specifically, when the cell adhesiveness (%) was less than 50%, the cell adhesiveness was evaluated as (−), that indicates a weak cell adhesiveness; when the cell adhesiveness (%) was not less than 50% and less than 90%, the cell adhesiveness was evaluated as (+), that indicates a stronger cell adhesiveness; and, when the cell adhesiveness (%) was not less than 90%, the cell adhesiveness was evaluated as (++), that indicates a still stronger cell adhesiveness.

TABLE 2

| | Sample | Phosphonic acid derivative | Carbon number of alkyl group in phosphonic acid derivative | Type of phosphonic acid derivative | Catechol derivative | Type of catechol derivative | Presence/ absence of polymer | Presence/ absence of anionic polymer or anionic compound | Presence/ absence of compound having sulfur element |
|---|---|---|---|---|---|---|---|---|---|
| Example 1 | 1 | ○ | 10 | Compound A | x | | ○ | x | ○ |
| | 2 | ○ | 10 | Compound A | x | | ○ | x | ○ |
| | 3 | ○ | 10 | Compound A | x | | ○ | x | ○ |
| Example 2 | 4 | ○ | 2 | Compound B | x | | ○ | x | ○ |
| | 5 | ○ | 2 | Compound B | x | | ○ | x | ○ |
| Example 3 | 6 | ○ | 10 | Compound A | x | | ○ | ○ | ○ |
| | 7 | ○ | 10 | Compound A | x | | ○ | ○ | ○ |
| | 8 | ○ | 2 | Compound B | x | | ○ | ○ | ○ |
| Comparative Example 1 | 9 | x | | | x | | x | x | ○ |
| Comparative Example 2 | 10 | ○ | 2 | Compound B | x | | ○ | x | ○ |
| | 11 | ○ | 10 | Compound A | x | | ○ | x | ○ |
| Comparative Example 3 | 12 | ○ | 10 | Compound A | x | | ○ | ○ | ○ |
| | 13 | ○ | 10 | Compound A | x | | ○ | ○ | ○ |
| Comparative Example 4 | 14 | x | | | x | | x | x | ○ |
| Example 4 | 15 | x | | | ○ | Compound C | ○ | x | ○ |
| | 16 | x | | | ○ | Compound D | ○ | x | ○ |
| | 17 | x | | | ○ | Compound E | ○ | x | ○ |
| | 18 | x | | | ○ | Compound F | ○ | x | ○ |
| Example 5 | 19 | x | | | ○ | Compound C | ○ | ○ | ○ |
| | 20 | x | | | ○ | Compound E | ○ | ○ | ○ |
| Comparative Example 5 | 21 | x | | | ○ | Compound C | ○ | x | ○ |
| | 22 | x | | | ○ | Compound E | ○ | x | ○ |
| Comparative Example 6 | 23 | x | | | ○ | Compound C | ○ | ○ | ○ |
| | 24 | x | | | ○ | Compound E | ○ | ○ | ○ |

| | Sample | Abundance ratio of sulfur element (atomic percent) | Abundance ratio of nitrogen element (atomic percent) | Weight average molecular weight of polymer | Carbon number of alkyl group in polymer | Anti-factor Xa activity after washing with physiological saline | Capacity to inhibit thrombus formation | Hemolytic toxicity |
|---|---|---|---|---|---|---|---|---|
| Example 1 | 1 | 3.0 | 9.2 | 750000 | 0 | + | + | − |
| | 2 | 3.2 | 9.1 | 750000 | 2 | ++ | ++ | − |
| | 3 | 3.3 | 9.0 | 750000 | 5 | ++ | ++ | − |
| Example 2 | 4 | 3.3 | 9.0 | 750000 | 2 | ++ | ++ | − |
| | 5 | 3.5 | 9.2 | 70000 | 2 | + + | + + | − |
| Example 3 | 6 | 5.1 | 9.5 | 600 | 2 | +++ | +++ | − |
| | 7 | 5.4 | 9.6 | 750000 | 2 | +++ | +++ | − |
| | 8 | 5.5 | 9.8 | 750000 | 2 | +++ | +++ | − |

TABLE 2-continued

| | | | | | | | | | |
|---|---|---|---|---|---|---|---|---|---|
| Comparative Example 1 | 9 | | | | | - | - | - | |
| Comparative Example 2 | 10 | 1.3 | 3.8 | 600 | 2 | - | - | - | |
| | 11 | 1.5 | 3.9 | 600 | 2 | - | - | - | |
| Comparative Example 3 | 12 | 6.9 | 14.2 | 750000 | 12 | +++ | +++ | + | |
| | 13 | 6.7 | 13.9 | 70000 | 12 | +++ | +++ | + | |
| Comparative Example 4 | 14 | | | | | - | - | - | |
| Example 4 | 15 | 3.2 | 8.8 | 750000 | 2 | ++ | ++ | - | |
| | 16 | 3.2 | 8.8 | 750000 | 2 | ++ | ++ | - | |
| | 17 | 3.0 | 9.0 | 10000 | 5 | ++ | ++ | - | |
| | 18 | 3.1 | 8.9 | 70000 | 5 | ++ | ++ | - | |
| Example 5 | 19 | 5.3 | 9.6 | 70000 | 2 | +++ | +++ | - | |
| | 20 | 5.2 | 9.5 | 70000 | 2 | +++ | +++ | - | |
| Comparative Example 5 | 21 | 1.3 | 3.7 | 600 | 2 | - | - | - | |
| | 22 | 1.2 | 3.6 | 600 | 2 | - | - | - | |
| Comparative Example 6 | 23 | 6.8 | 14.0 | 750000 | 12 | +++ | +++ | + | |
| | 24 | 6.6 | 13.8 | 70000 | 12 | +++ | +++ | + | |

TABLE 3

| | Sample | Cell adhesiveness | | Sample | Cell adhesiveness |
|---|---|---|---|---|---|
| Example 1 | 1 | ++ | Comparative Example 1 | 9 | ++ |
| | 2 | ++ | Comparative Example 2 | 10 | ++ |
| | 3 | ++ | Example 2 | 11 | ++ |
| Example 2 | 4 | ++ | Comparative Example 3 | 12 | - |
| | 5 | ++ | Example 3 | 13 | - |
| Example 3 | 6 | + | Comparative Example 4 | 14 | - |
| | 7 | + | Comparative Example 5 | 21 | ++ |
| | 8 | + | Example 5 | 22 | ++ |
| Example 4 | 15 | ++ | Comparative Example 6 | 23 | - |
| | 16 | ++ | Example 6 | 24 | - |
| | 17 | ++ | | | |
| | 18 | ++ | | | |
| Example 5 | 19 | + | | | |
| | 20 | + | | | |

INDUSTRIAL APPLICABILITY

The antithrombogenic metallic material can be used for medical devices (medical equipments and medical instruments) requiring continuous maintenance of high antithrombogenicity for a long period, in the field of medicine.

The invention claimed is:

1. An antithrombogenic metallic material comprising a metallic material having a surface coated with a non-hemolytic coating material,
said coating material comprising:
a phosphonic acid derivative or a catechol derivative;
a polymer containing, as a constituent monomer, a compound selected from the group consisting of alkyleneimines, vinylamines, allylamines, lysine, protamine, and diallyldimethylammonium chloride; and
an anionic compound containing a sulfur atom and having anticoagulant activity;
said polymer being covalently bound to said phosphonic acid derivative or said catechol derivative and said anionic compound being bound to said polymer by ionic bonding, and
said phosphonic acid derivative or said catechol derivative being bound to said metallic material through a phosphonic acid group or a catechol group thereof,
wherein an abundance ratio of nitrogen atoms to an abundance of total atoms as measured by X-ray photoelectron spectroscopy (XPS) on the surface coated with the coating material is 4.0 to 13.0 atomic percent, the phosphonic acid derivative is a carboxyalkylphosphonic acid or aminoalkylphosphonic acid, and the catechol derivative is a compound of General Formula (IV), a compound of General Formula (V), a compound of General Formula (VI), or a compound of General Formula (VII):

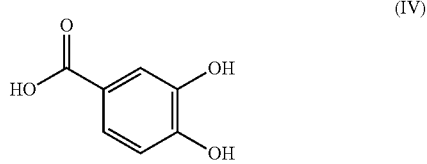

(IV)

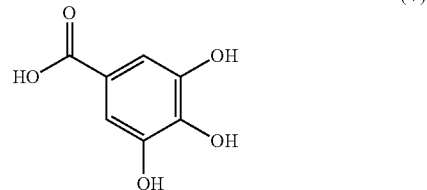

(V)

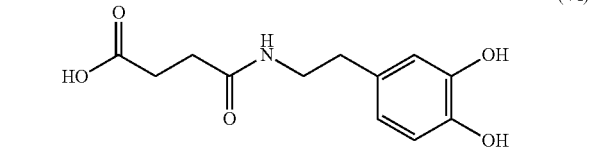

(VI)

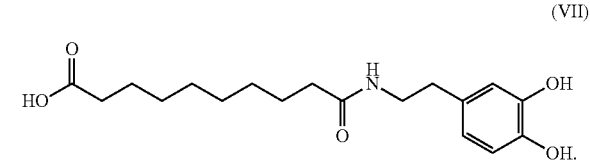

(VII)

2. The antithrombogenic metallic material according to claim 1, wherein an abundance ratio of sulfur atoms to the abundance of total atoms as measured by X-ray photoelectron spectroscopy (XPS) on the surface coated with the coating material is 3.0 to 6.0 atomic percent.

3. The antithrombogenic metallic material according to claim 1, wherein said polymer has a quaternary ammonium group.

4. The antithrombogenic metallic material according to claim 3, wherein each carbon chain bound to the nitrogen atom in said quaternary ammonium group comprises an alkyl group, and the carbon number per alkyl group is 1 to 12.

5. The antithrombogenic metallic material according to claim 1, wherein said coating material further comprises: an anionic polymer containing, as a constituent monomer, a compound selected from the group consisting of acrylic acid, methacrylic acid, α-glutamic acid, γ-glutamic acid, and aspartic acid; or an anionic compound selected from the group consisting of oxalic acid, malonic acid, succinic acid, fumaric acid, glutaric acid, adipic acid, pimelic acid, suberic acid, azelaic acid, sebacic acid, malic acid, tartaric acid, and citric acid.

6. The antithrombogenic metallic material according to claim 1, wherein said anionic compound containing a sulfur atom and having anticoagulant activity is heparin or a heparin derivative.

7. The antithrombogenic metallic material according to claim 1, wherein weight average molecular weight of said polymer is 600 to 2,000,000.

8. The antithrombogenic metallic material according to claim 1, wherein said metallic material is selected from the group consisting of iron, titanium, aluminum, tin, gold, silver, copper, platinum, chromium, cobalt, nickel, zinc, and tungsten; alloys thereof; and oxides and hydroxides of these metals.

9. An indwelling medical device produced from the antithrombogenic metallic material according to claim 1.

10. The antithrombogenic metallic material according to claim 2, wherein said polymer has a quaternary ammonium group.

11. The antithrombogenic metallic material according to claim 10, wherein each carbon chain bound to the nitrogen atom in said quaternary ammonium group comprises an alkyl group, and the carbon number per alkyl group is 1 to 12.

12. The antithrombogenic metallic material according to claim 2, wherein said coating material further comprises: an anionic polymer containing, as a constituent monomer, a compound selected from the group consisting of acrylic acid, methacrylic acid, α-glutamic acid, γ-glutamic acid, and aspartic acid; or an anionic compound selected from the group consisting of oxalic acid, malonic acid, succinic acid, fumaric acid, glutaric acid, adipic acid, pimelic acid, suberic acid, azelaic acid, sebacic acid, malic acid, tartaric acid, and citric acid.

13. The antithrombogenic metallic material according to claim 3, wherein said coating material further comprises: an anionic polymer containing, as a constituent monomer, a compound selected from the group consisting of acrylic acid, methacrylic acid, α-glutamic acid, γ-glutamic acid, and aspartic acid; or an anionic compound selected from the group consisting of oxalic acid, malonic acid, succinic acid, fumaric acid, glutaric acid, adipic acid, pimelic acid, suberic acid, azelaic acid, sebacic acid, malic acid, tartaric acid, and citric acid.

14. The antithrombogenic metallic material according to claim 4, wherein said coating material further comprises: an anionic polymer containing, as a constituent monomer, a compound selected from the group consisting of acrylic acid, methacrylic acid, α-glutamic acid, γ-glutamic acid, and aspartic acid; or an anionic compound selected from the group consisting of oxalic acid, malonic acid, succinic acid, fumaric acid, glutaric acid, adipic acid, pimelic acid, suberic acid, azelaic acid, sebacic acid, malic acid, tartaric acid, and citric acid.

15. The antithrombogenic metallic material according to claim 2, wherein said anionic compound containing a sulfur atom and having anticoagulant activity is heparin or a heparin derivative.

16. The antithrombogenic metallic material according to claim 3, wherein said anionic compound containing a sulfur atom and having anticoagulant activity is heparin or a heparin derivative.

17. The antithrombogenic metallic material according to claim 4, wherein said anionic compound containing a sulfur atom and having anticoagulant activity is heparin or a heparin derivative.

18. The antithrombogenic metallic material according to claim 5, wherein said anionic compound containing a sulfur atom and having anticoagulant activity is heparin or a heparin derivative.

19. The antithrombogenic metallic material according to claim 2, wherein weight average molecular weight of said polymer is 600 to 2,000,000.

20. The antithrombogenic metallic material according to claim 3, wherein weight average molecular weight of said polymer is 600 to 2,000,000.

* * * * *